US011615867B2

(12) United States Patent
    Lafon

(10) Patent No.: US 11,615,867 B2
(45) Date of Patent: Mar. 28, 2023

(54) MOLECULAR STRUCTURE EDITOR WITH VERSION CONTROL AND SIMULTANEOUS EDITING OPERATIONS

(71) Applicant: OpenEye Scientific Software, Inc., Santa Fe, NM (US)

(72) Inventor: Jharrod Lafon, Sante Fe, NM (US)

(73) Assignee: OPENEYE SCIENTIFIC SOFTWARE, INC., Santa Fe, NM (US)

( * ) Notice: Subject to any disclaimer, the term of this patent is extended or adjusted under 35 U.S.C. 154(b) by 387 days.

(21) Appl. No.: 16/685,681

(22) Filed: Nov. 15, 2019

(65) Prior Publication Data

US 2020/0160940 A1    May 21, 2020

Related U.S. Application Data

(60) Provisional application No. 62/768,047, filed on Nov. 15, 2018.

(51) Int. Cl.
    *G16C 20/90* (2019.01)
    *G16C 20/20* (2019.01)
(52) U.S. Cl.
    CPC ............. *G16C 20/90* (2019.02); *G16C 20/20* (2019.02)
(58) Field of Classification Search
    CPC ........ G16C 20/90; G16C 20/20; G16C 20/50; G16C 20/80
    See application file for complete search history.

(56) References Cited

U.S. PATENT DOCUMENTS

| 9,754,085 | B2* | 9/2017 | Clark ................... G06F 3/04883 |
| 10,605,773 | B2* | 3/2020 | Bleiholder .............. C40B 40/08 |
| 2010/0311598 | A1 | 12/2010 | Shapiro et al. |
| 2015/0370769 | A1 | 12/2015 | Pereira Filho |
| 2016/0321228 | A1 | 11/2016 | Thiesen et al. |
| 2017/0024451 | A1 | 1/2017 | Sullivan |
| 2017/0351846 | A1 | 12/2017 | Clark et al. |

OTHER PUBLICATIONS

Transmittal of the International Search Report and Written Opinion of the International Searching Authority dated, Jun. 15, 2020, for International Application No. PCT/US2019/061848, filed Nov. 15, 2019, pp. 7.

(Continued)

*Primary Examiner* — Manuel A Rivera Vargas
(74) *Attorney, Agent, or Firm* — Womble Bond Dickinson (US) LLP

(57) ABSTRACT

Computer-based methods that permit two or more users to perform simultaneous edits on a digitally encoded molecular structure. The methods use properties of conflict-free replicated data types (CRDT's) and causal trees to provide a distributed system which can manage the life-cycle of virtual molecular structures; including simultaneous editing, versioning, and provenance. Applications of the technology include, but are not limited to: simultaneous computer aided design of molecules in 2D or 3D in which users may be distributed across multiple computers and in which the need for computer time synchronization (offline or online editing) is obviated; version control and provenance tracking of a virtual molecule; and other types of data used in computer aided molecular design activities.

20 Claims, 10 Drawing Sheets

(56) References Cited

OTHER PUBLICATIONS

Transmittal of the International Search Report and Written Opinion of the International Searching Authority dated May 18, 2021, for International Application No. PCT/US2019/061848, filed Nov. 15, 2019, pp. 6.
Extended European Search Report for EP Application No. 19884232.0 dated Sep. 9, 2022.
Martin Kleppmann et al.: "A Conflict-Free Replicated JSON Datatype", arxiv.org, Cornell University Library, 201 Olin Library Cornell University Ithaca, NY 14853, Aug. 13, 2016, pp. 1-16.
Imae Kengo et al.: "ChainVoxel: A Data Structure for Scalable Distributed Collaborative Editing for 3D Models", 2016 IEEE 14th Inti Conf on Dependable, Autonomic and Secure Computing, 14th Inti Conf on Pervasive Intelligence and Computing, 2nd Inti Conf on Big Data Intelligence and Computing and Cyber Science and Technology Congress, Aug. 8, 2016, pp. 344-351.
Marc Shapiro et al.: "Conflict-Free Replicated Data Types", Oct. 10, 2011, pp. 386-400.
Marcus D Hanwell et al.: "Open Chemistry: RESTful Web APIs, JSON, NWChem and the Modem Web Application", arxiv.org, Cornell University Library, 201 Olin Library Cornell University Ithaca, NY 14853, Jul. 13, 2017, pp. 1-14.
Chen Zhao et al.: "A Collaboration Transparence Approach to Share Heterogeneous Single-User Molecule Editors", Procedia Environmental Sciences, vol. 8, 2011, pp. 319-327.
Ruipeng Wei et al.: "Design and Implementation of Scientific Collaborative Editing Environment on Chemistry", 2009 Eighth International Conference on Grid and Cooperative Computing, Aug. 27, 2009, pp. 188-192.
Dongmei Yue et al.: "Domain-Specific Groupware Environment for E-research on Chemistry", 9th IEEE/ACM International Symposium on Cluster Computing and the Grid, May 18, 2009, pp. 591-596.

\* cited by examiner

S1@12[CH4]1[CH4][CH4][CH4][CH4][CH4]1

S2@16[CH4][OH2][CH4](1[CH4][CH4]([CH4][CH4]1)[NH4+]

MOLECULAR STRUCTURE EDITOR WITH VERSION CONTROL AND SIMULTANEOUS EDITING OPERATIONS

CLAIM OF PRIORITY

This application claims the benefit of priority under 35 U.S.C. § 119(e) to U.S. provisional application Ser. No. 62/768,047, filed Nov. 15, 2018, which is incorporated herein by reference in its entirety.

TECHNICAL FIELD

The technology described herein generally relates to computer-based manipulations of molecular structure data, and more particularly relates to methods that permit multiple users to perform editing operations on a molecular structure, stored digitally, without conflict and with version control.

BACKGROUND

The drug discovery process—for many years a largely empirical exercise—benefits today from a host of computational tools for building, altering, and analyzing molecular structures. These tools are not used exclusively by computer scientists but may also be used by laboratory chemists and project leaders. In any given project, a large number of researchers may have access to the computer-stored molecular structure data, and many members of the development team may introduce new data or may make changes to existing data.

In short, the process of developing a new drug molecule relies heavily on a variety of computational tools that enable researchers to quickly perform a number of functions that go hand in hand with the experimental steps of testing and creating new molecular structures. Such functions include: visualizing 2 and 3-dimensional molecular structures on a computer display; exploring binding interactions between pairs of molecules, such as through simulations of dynamics or through building virtual models of ligand-receptor complexes; searching databases of thousands or millions of digitally encoded molecular structures; and refining the structures of promising molecules through computational manipulation.

All of these functions rely on a consistent computer-representation of a molecular structure in which atom types and the bonds between them are stored in a standard format. Correspondingly, with a commonly understood digital representation of chemistry, it becomes possible to perform mutations of molecular structure data, as a surrogate for exploring the same or comparable changes on real molecules, with great ease.

In practice, however, the computer aided molecular design process frequently involves multiple parties proposing and making iterative changes to molecular structure data. Any computer-based system that allows multiple parties to edit the same data, in this case one or more molecular structures, must have a method for coordinating the edits. Specifically, it is undesirable for two persons to introduce conflicting edits to the same structure, and it can be useful to track sequences of edits by multiple parties in such a way that a given edit can be traced to a particular editor at a particular time-stamp.

For example, concurrent sets of edits to replicas of the same data distributed on different computers but without coordination, can result in a violation of atomic consistency from the set of ACID properties (see, for example, "The Transaction Concept: Virtues and Limitations", Jim Gray).

ACID is an acronym for a set of properties (atomicity, consistency, isolation, and durability), typically in the context of databases, that are related to the idea of a transaction. Relational and non-relational databases are widely used technologies for managing data in a shared computing system. If an ordered set of database operations fulfill the ACID properties, then they are said to be a transaction. Atomicity is one of the ACID properties that is emphasized herein in the context of molecular editing. The Atomicity property is desirable because it guarantees that edits (or sets of edits) are never partially applied.

In full, the ACID properties are as follows:
Atomicity means that each transaction is applied as a unit and succeeds completely or fails completely; a failed transaction must leave the database unchanged.
Consistency means that a transaction brings the database from one valid state to another, so that there can be no corruption of the database due to an invalid transaction.
Isolation allows concurrently executing transactions to have well defined behavior, where the level of isolation determines when the resulting state of one transaction is visible to another.
Durability means that once a transaction has been executed (said to be committed), the resulting state may not be lost. In this sense, where durability exists, transactions are said to be durable, The fact that most computer systems are now network-based compounds the difficulty. Whereas tracking editing operations performed on a single computer—even by different users—may be tractable, the reality of research today, in which data may be stored centrally but is accessible from hundreds or thousands of networked computers at any one time, makes the management of simultaneous edit operations on a molecular structure a challenging problem. The problem is no easier if the data is not stored centrally but instead is disseminated to multiple computers in a given network, each of which provides the capability to a different user to manipulate the data, often concurrently with one another.

Molecular structure data in particular is different from text-based document data for at least two reasons: there are issues of provenance and the structure of edits that make molecular structure data unique.

Provenance is important because it is generally useful to be able to determine how a given molecular structure came to be. This information can be used to inform scientists about the effectiveness of their overall process of molecular design, to recognize trends in edits that are applied to multiple structures, or determine if a part of chemical space should have been explored but wasn't. (For example, a set of edits was used in project X which resulted in a useful outcome, but only a subset of the edits used in project X were used in a different project). Thus, it is useful to know the provenance of the fragments of a molecule. This contrasts with textual data, which isn't generally useful in fragments (for example, the word "the" as a fragment on its own is not informative).

The structure of edits to molecular data is unique and markedly different to the types of editing operations that are applied to text. For example, text is interpreted in a deterministic order and without cyclic relationships. Any given character in a document occurs either at the beginning, or after another character. In contrast, it is quite common for molecules to contain one or more rings.

Coordination of edits to computer-stored data, in general, is possible through concurrency control schemes, but such schemes introduce overhead and are limited in their scalability. (Concurrency control is a term used to describe a class of methods which provide a deterministic outcome in the presence of simultaneous altering of data in a computing system. Concurrency control schemes often rely on the majority consensus of participants or distributed locking.) More importantly, while coordination provides consistency, it does not preserve the history of edits that may have conflicted with one another. Thus, concurrency control schemes technically resolve conflicts in the sense that a deterministic result is achieved, but the intent of the edits may be lost, depending on how the conflicts are resolved. Thus, if two parties store concurrently a value in the same row of a database, that may result in the value stored being that of the last committed transaction, rather than a value representing a merger of the two values. For example, if two researchers attempt to concurrently attach two different functional groups to the same attachment points on a shared molecular structure, those edits are in conflict and must be resolved. Even assuming that a method can be devised to resolve such conflicts, the resulting state of the resolved molecule is still subject to conflict if another edit has been made concurrent to the conflict resolution.

Accordingly, there is a need for a method of reliably managing concurrent edits to molecular structure data so that users can confidently carry out edits to a given molecular structure without conflicting with one another.

The discussion of the background herein is included to explain the context of the technology. This is not to be taken as an admission that any of the material referred to was published, known, or part of the common general knowledge as at the priority date of any of the claims found appended hereto.

Throughout the description and claims of the instant application the word "comprise" and variations thereof, such as "comprising" and "comprises", is not intended to exclude other additives, components, integers or steps.

SUMMARY

The instant disclosure is directed to a computer-based method and apparatus for simultaneous, versioned, editing of molecular structure data by two or more users. The disclosure further comprises a computer-readable medium encoded with instructions for performing such methods. The apparatus and process of the present disclosure are particularly applicable to a drug development environment in which many researchers are accessing the same molecular structure data and making or suggesting edits to the same.

The methods herein rely upon depiction of molecular structures as undirected graphs, and individual users as sites associated with the graphs. Lamport logical clock, Lamport timestamps, and conflict free replicated data types are utilized to ensure that edits performed by two or more users do not conflict with one another.

BRIEF DESCRIPTION OF THE DRAWINGS

The present invention is illustrated by way of example and not limitation in the figures of the accompanying drawings in which like references indicate similar elements. The appended figures demonstrate aspects of simultaneous editing of a molecular structure. The figures comprise a depiction of a molecular structure, and the corresponding causal tree. The atoms are labeled with a globally unique timestamp constructed in the form SITE_ID@LAMPORT_TIMESTAMP. A molecule's latest timestamp and SMILES string are shown above the respective depictions. The labels on causal tree nodes show the details of the edit. The arrows within a causal tree indicate a causal relationship, pointing from causal parent to causal child.

DETAILED DESCRIPTION

Figure 1:
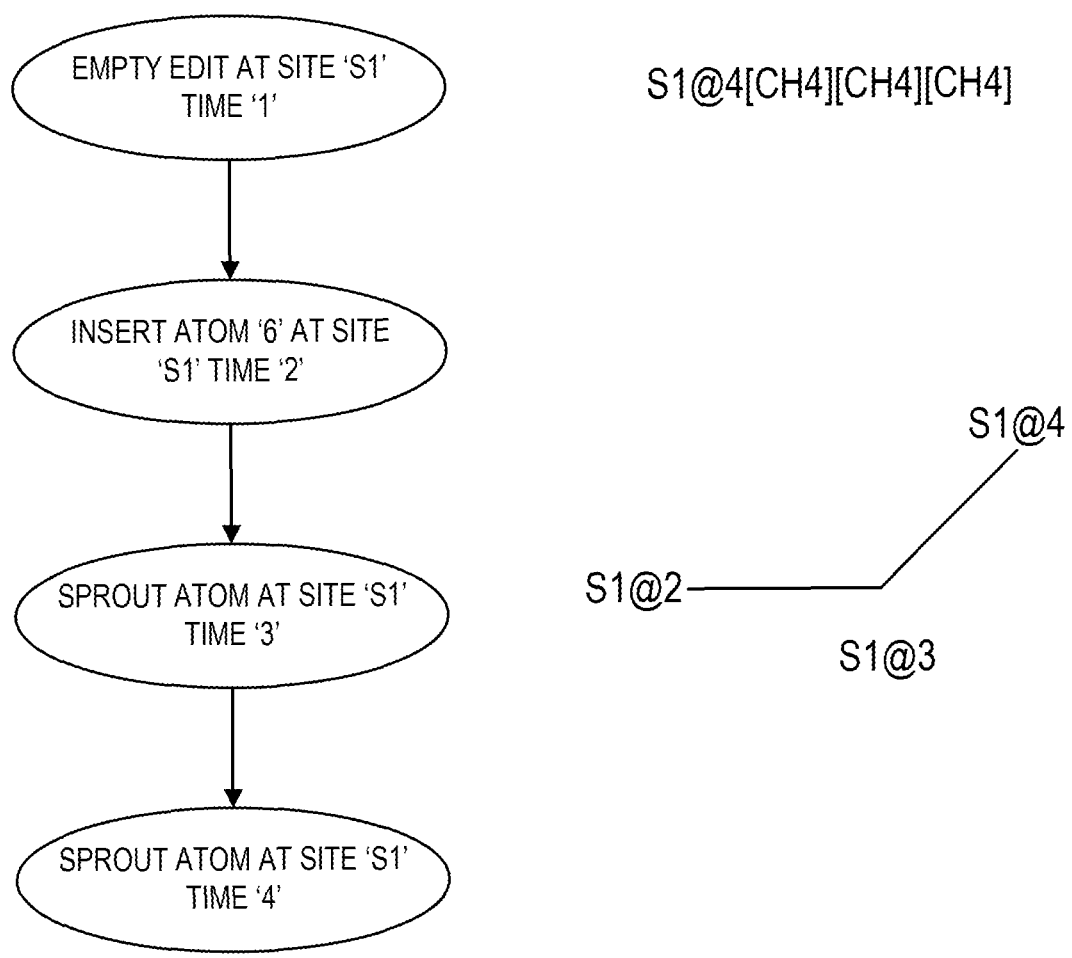
FIG. 1 is an illustration of one embodiment of a simple causal tree for edits made at a site 'S1'.

The instant technology is directed to a computer-based system for permitting two or more parties to make concurrent edits on a digitally stored representation of a molecular structure, without introducing conflicting edits.

Methodology

The following is an exemplary description of an implementation of a method, executed by a suitably configured computer system for carrying out simultaneous, versioned, editing of molecular structures. It would be understood that in each aspect of the methodology, the description herein is neither exclusive, restrictive, nor limiting and that other comparable aspects could be identified by those skilled in the art without departing from the novelty, inventiveness, or operating principles of the method. Such methodology will find application in computer-aided molecular design situations.

Data structures employed by the method include, but are not limited to: a set of undirected graphs where each graph represents a virtual set of molecular structures because each structure can be edited and each edit can be thought of as a new molecule; a set of labeled vertices for each graph, where each vertex represents an atom; a set of labeled edges for each graph, where each edge represents a bond; a set of sites, each representing an interactive user.

Each site in the set of sites that represent an interactive user comprises: a globally unique site identifier; an operational array of edits; one or more messages containing operational arrays and Lamport timestamps which can be exchanged with other sites; and a Lamport logical clock (see, for example, "Time, Clocks, and the Ordering of Events in a Distributed System", Leslie Lamport, available on the World-wide-web at: lamport.azurewebsites.net/pubs/time-clocks.pdf).

A set of Lamport logical clocks, one for each site, is such that: a site increments its clock before making an edit, which guarantees that two edits in the same site never have the same clock value; a site includes its clock value in or with messages that it sends to other sites; a site updates its clock when receiving a message from another site to the greater of its own clock value or the clock value included in the message, and then increments its own clock. In one embodiment, each site maintains its own logical clock (e.g., a Lamport clock). In this embodiment, the site can be a client, or a process of the client that views and/or edits a molecule structure.

Edits can be handled in the following manner. The data structure employed can comprise an ordered set of edits, where each of the edits represents a mutation to a particular graph. In this scheme, each edit can include one or more of the following: a unique identifier that includes the identifier of the site where the edit was created, and a Lamport timestamp for the edit's creation from the originating site's Lamport logical clock; an edit type from a set of predefined edits; the identifier of the edit's parents, which defines a causal relationship between the edit and its parents; and a cryptographic signature which can be used to verify that authorship of the edit.

The set of predefined edits generally comprises types of edit operations that a molecular modeler would normally apply to a molecular structure represented in digital form on a computer. Thus, the predefined edits include at least the following:
1. add_root_atom: an edit which inserts the first atom into an empty molecule;
2. sprout: an edit which adds both an atom and a bond to a molecule, where the bond is between the newly added atom and an existing atom;
3. add_bond: an edit which inserts a bond between two existing atoms;
4. delete_bond: an edit which deletes an existing bond;
5. delete_atom: an edit which deletes an existing atom; and Other edits upon an atom or bond may also be defined. For example, an edit that changes the formal charge, protonation, or some other property of an atom may be defined. Similarly, an edit that changes a bond order (such as from single to double) may be defined.

The ordered set of edits previously described can further comprise an operational array that permits store causal relationships to be stored, wherein: the array corresponds to one molecular graph; each new array is initialized with an empty edit, which is the root of all subsequent edits; edits in the array are ordered by their Lamport timestamps; edits in the array may have parent or child links to other edits; one or more operational arrays may merge; and/or a causal tree may be computed from the operational array by performing a depth-first preorder traversal beginning at the first array element.

It would be understood that an appropriate ordering of edits in the operational array is as follows: for any given events A and B, causal ordering is provided such that A is said to have happened before B if A's Lamport timestamp is less than B's, and two or more edits with the same timestamp, but originating from different sites, are ordered by their originating site identifiers (which are necessarily unique).

It would further be understood that, when one or more operational arrays are merged, the merge is such that merges are performed without conflicts, resulting in a deterministic merged array order, and merges on a set of arrays may be performed in any order but produce the same result.

Causal trees in the exemplary data structure can each be constructed from an operational array such that: each node is an edit from the operational array; and the depth-first preorder traversal of the causal tree may be used to apply all edits in a deterministic order. A suitable deterministic order is: a node's children are explored in descending order of Lamport timestamps; sibling branches represent concurrent edits, and are logical forks of a molecule; subtrees are consecutive edits.

The implementation of a molecular structure editor as described herein may further comprise a multi-user interface for viewing and editing sets of molecular structures having some or all of the following capabilities:
1. each user's interactive session is implemented as a new site;
2. one or more users may view and edit the same molecular structure which is backed by an operational array;
3. users may make edits (with or without connectivity) concurrently on an operational array;
4. edits are exchanged with other sites (or a centralized server) by message passing, where the messages contain the site's operational arrays;
5. all versions of a particular structure may be viewed and edited by iterating through the operational array;
6. conflicting concurrent edits to a particular edits may be resolved, resulting in new edits in the operational array; and
7. chemically impossible configurations of the structure's graph are visually indicated along with the identity of each edit's author.

Conflict-Free Replicated Data Types

Conflict-free Replicated Data Types (CRDT's) are a name given to a class of data structure which fulfills a set of properties, rather than a specific data structure, and so a particular CRDT must be designed for purpose. In particular, and in one embodiment, CRDTs are data structures that avoid conflicting edits by design. These data structures can be replicated across distributed systems and mutated concurrently without coordination of the participants. Gossip protocols, or peer to peer communication, may be used to disseminate changes to the data. When a participating computer receives an update to its own replica of the CRDT, the merge is applied without conflict. The result of the merged update is provably deterministic so long as each participating computer eventually receives the update. Because the updates to CRDT's and their merger with replicas are provably commutative and conflict-free, concurrent edits do not require coordination.

CRDT's, which have previously found application to text data, can be usefully deployed in molecular structure editing because they provide appropriate provenance for series of edits, and also permit handling the types of complex edits that apply to molecular structures.

Molecular structure data and text data have different characteristics from one another. Therefore, CRDTs designed for text editing are not useful for representing molecular data because the fundamental relationships within the data are different. For example, because text fragments on their own are not useful, a CRDT applied to text editing has no need to compute the provenance of a fragment. In contrast, a molecular CRDT which provides fragment provenance may be useful in successive drug discovery projects. As mentioned above, sets of molecular CRDTs may be mined to find useful information about edits that are applied across projects. Additionally, and because CRDTs may be merged idempotently, libraries of edits can be computed ahead of time and then applied as necessary. (As would be understood by those skilled in the art, idempotence is a property which guarantees that the operational array—and its corresponding causal tree—which is the result of merging a set of operational arrays any number of times, is identical to the result of merging the same arrays exactly once. This merger is independent of time, so one can use common sets of existing edits (such as might be mined from a corporate database) and apply them at any point in time.)

Furthermore, molecular structures contain rings and are not simply linear strings of data. By contrast, characters in a text document have a specific order, and that order is often used as the basis for a causal ordering in a text CRDT. However, any given atom in a ring within a molecule does not have an obvious causal parent, as any ring atom has at least two potential causal parents. In one embodiment, edits in the molecular CRDT described herein can be customized to overcome this potential ambiguity. For example, certain edits, such as the insertion of a bond, are permitted to have more than one causal parent (as shown, for example, in the figures for timestamp S1@12).

At their core, CRDTs rely on the concept of a join semi-lattice. The following is a high level overview of a join semi-lattice for a set of edits (S) on a CRDT. An order is a binary relation $\leq$ on S: $<S,\leq>$. For any x,y in a set S, the join x\/y is the least upper bound of S according to $<S,\leq>$. A join semi-lattice is an order $<S,\leq>$ for which there exists a join x\/y for any x,y$\in$S. In the distributed system, edits may be created by any member of the system. Lamport timestamps may be used to provide the partial ordering for edits.

Molecule CRDT

A distributed system is defined as a set of communicating peers, called sites. Each site (which has a globally unique identifier) has a replica of the molecule CRDT and logically represents an end user concurrently editing the shared molecule. Lamport timestamps are attached to each molecule edit and are used to provide a partial ordering necessary for the CRDT, with the sites implementing the Lamport timestamp algorithm. Edits with an identical timestamp are ordered by their originating site's identifier. Sites may make edits and exchange their replicas using a gossip protocol, peer to peer protocol, or by committing the replica to durable storage to be read by other sites.

In one embodiment, the representation of a molecule by a CRDT is referred to as a CRDTMol. Each new CRDTMol is initialized with an empty edit operation, which will be the causal parent initial edits. The CRDTMol is implemented as an operational array which contains the ordered set of immutable edits. Each edit in the array has an identifier which is unique within the array, consisting of the originating site's ID and the Lamport timestamp of the edit's creation. Edits have an edit_type which defines the nature of the edit, as well as auxiliary data for the edit. Edits also store references to their causal parents and children. The references between edits, beginning at the first empty edit, form a causal tree.

Each site implements a user interface for interacting with the molecule, which internally interacts with the CRDTMol. Every atom and bond in the molecule displayed maintains a reference to the edit which caused that entity to exist.

Creating Edits

New edits are created on a site in the following manner. Depending on the type of the edit, the edit's causal parents are determined.
1. For 'add_root_atom' the causal parent is the first (empty) edit of the operational array.
2. For 'sprout' the causal parent is the edit which caused the atom to which the new atom is bonded to exist.
3. For 'add_bond' there are two causal parents which are the edits which caused the bonded atoms to exist.
4. For 'delete_bond' there are two causal parents which are the edits which formerly caused the bonded atoms to exist.
5. For 'delete_atom' the causal parent is the edit which caused the atom to exist.

The logical Lamport clock of the edit is incremented. The new edit is created with parental references, using the incremented timestamp. Finally, the edit is appended to the operational array.

Computing a Molecule from a Causal Tree

At any time, a site may compute the state of a molecule from the causal tree by applying edits from the causal tree in depth-first preorder. During traversal, siblings are sorted in descending timestamp order. Edits are applied in causal order with graph vertices and edges being created iteratively. Note that any version of the molecule, including forks may be constructed by traversing the corresponding subtree.

Figure 8:
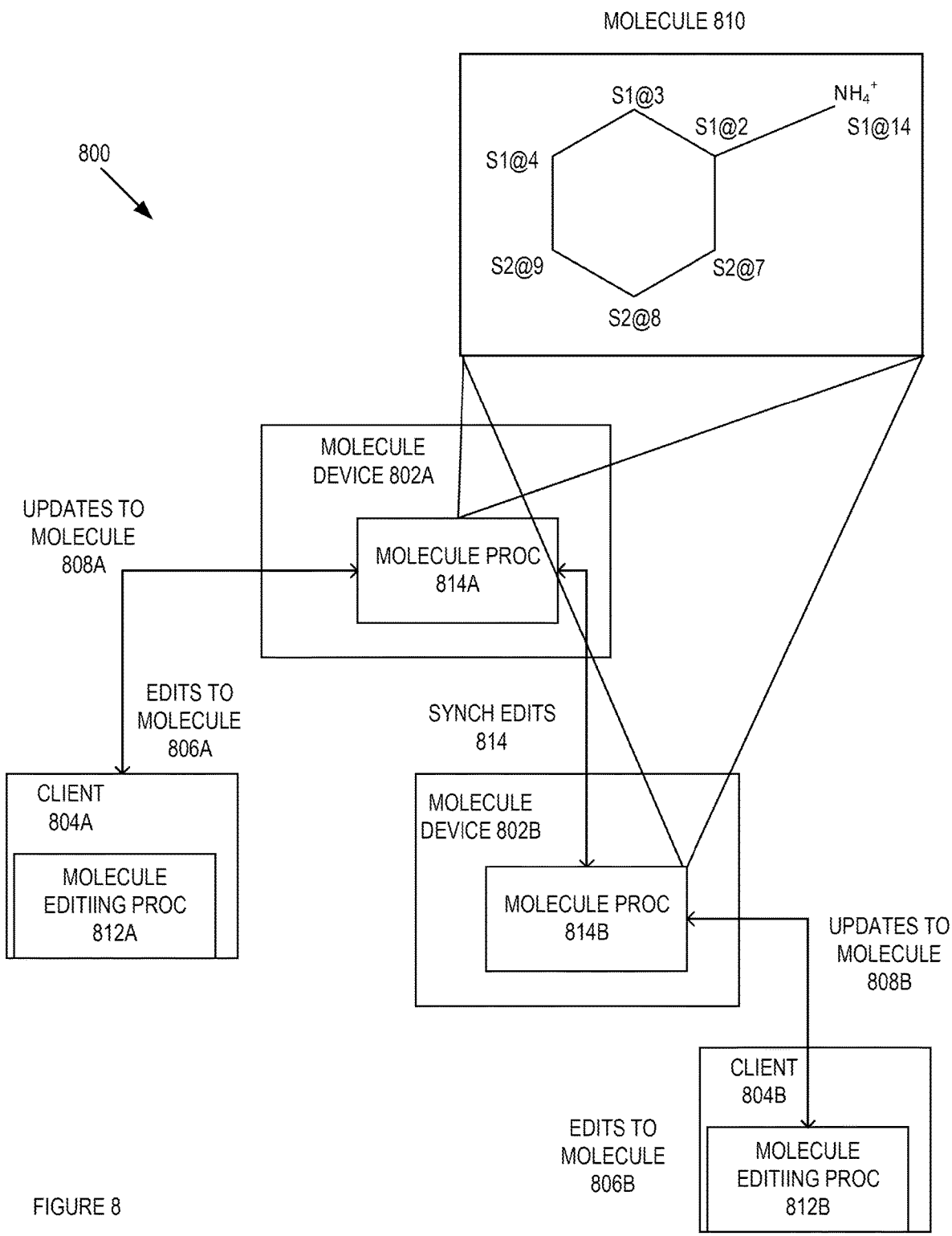
FIG. 8 is a block diagram of one embodiment of a system that supports concurrent edits to a molecular structure.

FIG. 8 is a block diagram of one embodiment of a system 800 that supports concurrent edits to a molecular structure. In FIG. 8, the system 800 includes a molecule device 802A coupled to another molecule device 802B and each of these molecule devices 802A-B are coupled to a respective client 804A-B. In one embodiment, each of the molecule editor devices 802A-B is a device that hosts a molecule process 814A-B that can support editing of a molecule 810 without the need for locks on the molecule as a whole or parts of the molecule that would prevent other clients from performing concurrent edits to that molecule 810. This allows users of the two clients 804A-B to concurrently edit the molecule without the need for locking changes to the molecule when one of the clients is editing this molecule 810. In one embodiment, each of the molecule device 802A-B can be a personal computer, laptop, server, mobile device (e.g., smartphone, laptop, etc.), network element, and/or any device capable of computing and maintaining a molecular structure. In addition, each of the clients 804A-B independently can be a personal computer, laptop, server, mobile device (e.g., smartphone, laptop, etc.), network element, and/or any device capable of receiving and presenting a molecular structure. In addition, each of the molecule devices 802A-B and/or clients 804A-B can be a physical or virtual device. While in one embodiment, two molecule devices 802A-B and two clients 804A-B are illustrated, in alternate embodiment, there can independently be more or less numbers of the molecule editor device and/or clients.

For example and in one embodiment, there can be a plurality of servers acting as molecule devices that concurrently receive edits from respective clients, where each of the molecule servers replicate the edits to the other molecule servers so as to arrive at an eventual consistency of the molecule 810 for each of the client viewing the molecule 810. Thus, in this example, if one of the clients generates an edit to the molecule 810, this edit is propagated from the receiving molecule server coupled to this client to the other molecule server(s), which in turn push the edit to the other clients viewing this molecule. In addition, during this time, another client can generate an edit, which is also propagated to the other clients. Thus, in this example, edits can appear in one client as that client is making edits to the same molecule 810. In this example, the client can briefly lock edits to the molecule structure for the user of this client while remotely generated edits are being applied to the molecule. However, in this example, this lock is not applied to other clients.

In one embodiment, each of the clients 804A-B includes a molecule editing process 812A-B that supports concurrent editing of the molecular structure of the molecule 810. In this embodiment, the molecule editing process 812A-B generates edits to the molecule structure 810 in response to actions of a user and stores those edits in a molecule conflict-free replicated data type (e.g., a CRDTMol) as described above. The molecule editing process 812 further can send updates 808A-B to the edits back to the corresponding molecule device 801A-B as needed. In one embodiment, each of the clients 804A-B include a web browser that is used to display and generate the edits to the molecule 810. In this embodiment, the molecule editing process 812A-B integrates the edits from the respective clients 804A-B and presents updates so that updated molecule 810 can be displayed in the web browser of the clients 804A-B. For example and in one embodiment, client 804A can add the functional group $NH_4^+$ to the molecule 810 while the client 804B is concurrently viewing and/or editing the molecule 810. This edit is captured by the molecule editing process 812A, where the edit is integrated into the CRDTMol for the molecule 810 on client 804A, and this edit is reflected back to the client 804B. In one embodiment, each of the clients 804A-B and the molecule device 802A-B maintain a CRDTMol for the molecule 810, where the molecule devices 802A-B send edit updates to the clients 804A-B propagated by the molecule devices 802A-B. Each client 804A-B that receives an edit update integrates this edit update into the CDRTMol maintained by the client 804A-B.

Figure 9:
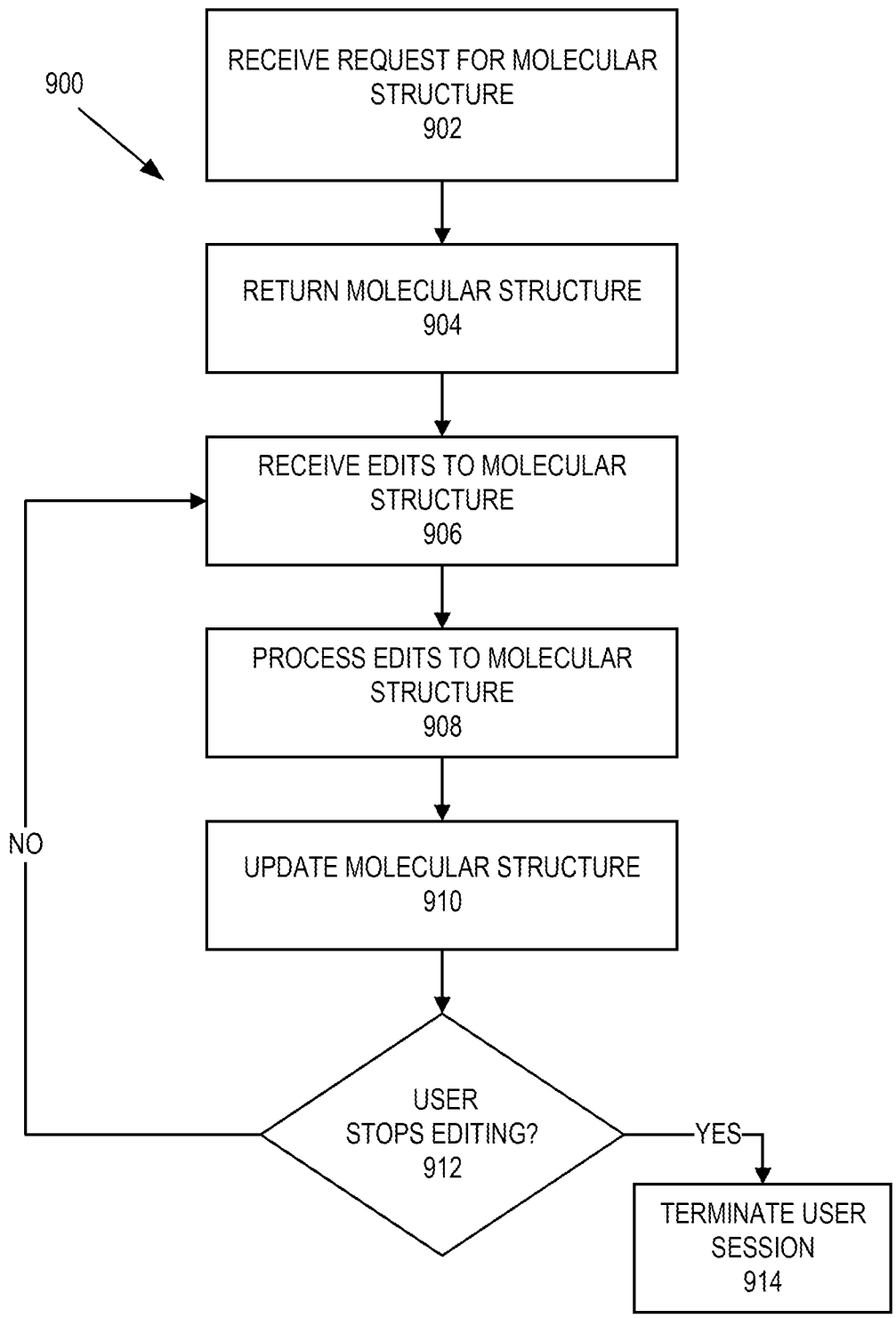
FIG. 9 is a flow diagram on one embodiment of a process to support concurrent edits to a molecular structure.

FIG. 9 is a flow diagram on one embodiment of a process 900 to support concurrent edits to a molecular structure. In one embodiment, process 900 is performed by a molecule editing process, such as the molecule editing process 812A-B as described in FIG. 8 above. In FIG. 9, process 900 begins by receiving a request for a molecular structure at block 902. In one embodiment, a user can indicate an interest in editing the molecular structure using a client as describe in FIG. 8 above. In another embodiment, the user has started an editing session with process 900 (e.g., logged in with a user account). At block 904, process 900 receives the molecular structure. In one embodiment, process 900 receives the molecular structure using a web protocol to a web browser (e.g., a client makes a Hypertext Transfer Protocol (HTTP) request for the molecular structure to the molecule device and the molecule device responds to the request by sending the molecular structure in a combination of Hypertext Markup Language, JavaScript, and/or other data to the client).

Process 900 receives one or more edits to the molecular structure from the user at block 906. In one embodiment, the edits can be an atom addition/deletion and/or bond addition/deletion. In a further embodiment, one of the edits can be locally generated from the user actively editing the molecule using the client or can be a remotely generated edit received from another client that is propagated via one or more of the molecule devices as described in FIG. 8 above. At block 908, process 900 processes the received one or more edits to the molecular structure. In one embodiment, process 900 processes each of the locally generated edits by timestamping this edit using a Lamport timestamp as described above. In this embodiment, each of the edits for the molecular structure (including any previously received edits) will have a different timestamp (e.g., by using a Lamport timestamp as described above). In addition, process 900 can cryptographically sign each edit so as to associate this edit with a particular user as described above. The remotely generated edits that have been received from one of the molecule devices will have been processed by the client that generated the edit, so each of the remotely generated edits will have its own timestamp and/or other information (e.g., cryptographic sign, site identifier, and/or other information). Furthermore, process 900 can process the edit using any of the actions, alone or in combination, described above. Process 900 updates the molecular structure using the edits at block 910. In one embodiment, process 900 updates the molecular structure by integrating the processed edits into the CRDT-Mol for the molecular structure. In addition, process 900 sends the locally generated edits to molecule device, which propagates these edits so that other clients can have an updated copy of the CDRTMol.

At block 912, process 900 determines the user stops editing the molecular structure. If a user does stop editing, process 900 terminates the user session at block 914. If not, execution proceeds to block 906 above.

Figure 10:
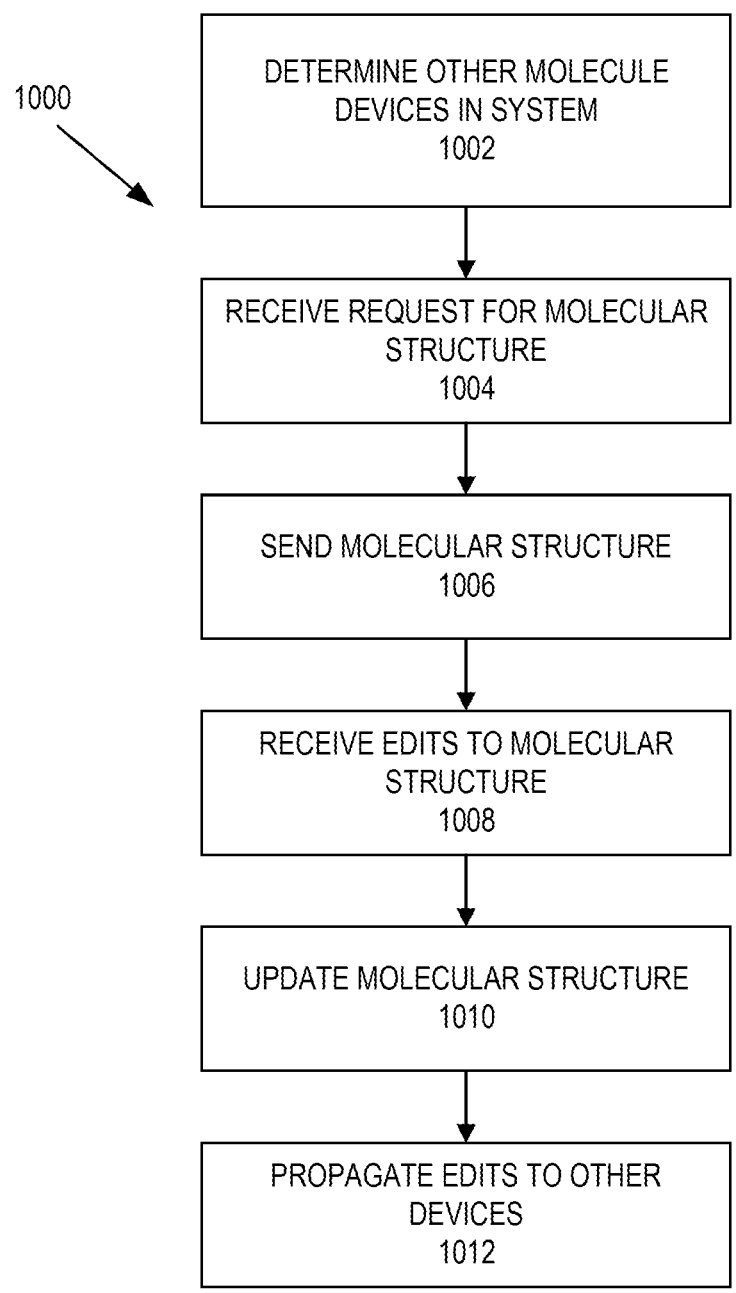
FIG. 10 is a flow diagram of one embodiment of a process to propagate edits to a molecule structure to one or more clients.

FIG. 10 is a flow diagram of one embodiment of a process 1000 to propagate edits to a molecule structure to one or more clients. In one embodiment, process 1000 is performed by a molecule process to propagate molecule structure edits, such as the molecule process 814A-B as described in FIG. 8 above. In FIG. 10, process 1000 begins by determining other molecule devices in the system at block 1002. In one embodiment, there can be multiple molecule devices that are used to propagate edits to one or more molecule structures. In this embodiment, clients will communicate with one of the molecule devices, so as to receive and send edit to a molecule structure.

At block 1004, process 1000 receives a request for a molecule structure. In one embodiment, a client will send a request for the molecule structure. Process 1000 sends the molecule structure at block 1006. At block 1008, process 1000 receives edits to the molecule structure. In one embodiment, the edits can be locally generated or remotes generated, where locally generated edits are from a client coupled to the molecule device executing process 1000 and remotely generated edits are edits received from another molecule device. Process 1000 updates the molecule structure maintain by process 1000 at block 1010. In one embodiment, process 1000 maintains a CRDTMol for the molecule structure and process 1000 updates this CRDTMol as described above. At block 1012, process 1000 propagates the edits to other devices. In one embodiment, for locally generated edits, process 1000 propagates the edits to other molecule devices known in the system. In another embodiment, for remotely generated edits, process 1000 propagates the edits to the client and other molecule devices (as needed). If process 1000 has received the edit previously, process 1000 does not propagate that edit.

Implementation Details

The methods described herein are preferably implemented on one or more computer systems, and the implementation is within the capability of those skilled in the art. In particular, the computer functions for manipulations of molecular structures, can be developed by a programmer skilled in the art. The functions can be implemented in a number and variety of programming languages including, in some cases, mixed implementations (i.e., relying on separate portions written in more than one computing language suitably configured to communicate with one another). For example, the functions, as well as any required scripting functions, can be programmed in C, C++, Java, JavaScript, VisualBasic, Tcl/Tk, Python, Perl, .Net languages such as C#, and other equivalent languages. The capability of the technology is not limited by or dependent on the underlying programming language used for implementation or control of access to the basic functions. Alternatively, the functionality could be implemented from higher level functions such as tool-kits that rely on previously developed functions for manipulating data structures.

Where two or more parties separately and independently perform computations, such as editing operations on molecular structure data, it is to be assumed that each party independently has access to a computer system that has the capability described herein, even though the various computer systems operated by the various parties need not be identical to one another in power or in the precise details of the manner in which they are programmed.

The technology herein can be developed to run with any of the well-known computer operating systems in use today, as well as others not listed herein. Those operating systems include, but are not limited to: Windows (including variants such as Windows XP, Windows95, Windows2000, Windows Vista, Windows 7, and Windows 8 (including various updates known as Windows 8.1, etc.), and Windows 10, available from Microsoft Corporation); Apple iOS (including variants such as iOS3, iOS4, and iOS5, iOS6, iOS7, iOS8, and intervening updates to the same); Apple Macintosh operating systems such as O59, OS 10.x, OS X (including variants known as "Leopard", "Snow Leopard", "Mountain Lion", "Lion", "Tiger", "Panther", "Jaguar", "Puma", "Cheetah", "Mavericks", and "Yosemite"; the UNIX operating system (e.g., Berkeley Standard version) and variants such as IRIX, ULTRIX, and AIX; and the Linux operating system (e.g., available from Red Hat Computing).

To the extent that a given implementation relies on other software components, already implemented, such as functions for establishing and modifying data structures, and displaying molecular structure data on a computer display, those functions can be assumed to be accessible to and modifiable by a programmer of skill in the art.

Furthermore, it is to be understood that the executable instructions that cause a suitably-programmed computer to execute methods for carrying out concurrent edits to a molecular structure, as described herein, can be stored and delivered in any suitable computer-readable format. This can include, but is not limited to, a portable readable drive, such as a large capacity "hard-drive", or a "pen-drive", such as can be connected to a computer's USB port, and an internal drive to a computer, and a CD-Rom, or an optical disk. It is further to be understood that while the executable instructions can be stored on a portable computer-readable medium and delivered in such tangible form to a purchaser or user, the executable instructions can be downloaded from a remote location to the user's computer, such as via an Internet connection which itself may rely in part on a wireless technology such as WiFi. Such an aspect of the technology does not imply that the executable instructions take the form of a signal or other non-tangible embodiment. The executable instructions may also be executed as part of a "virtual machine" implementation.

Computing Apparatus

Figure 7:
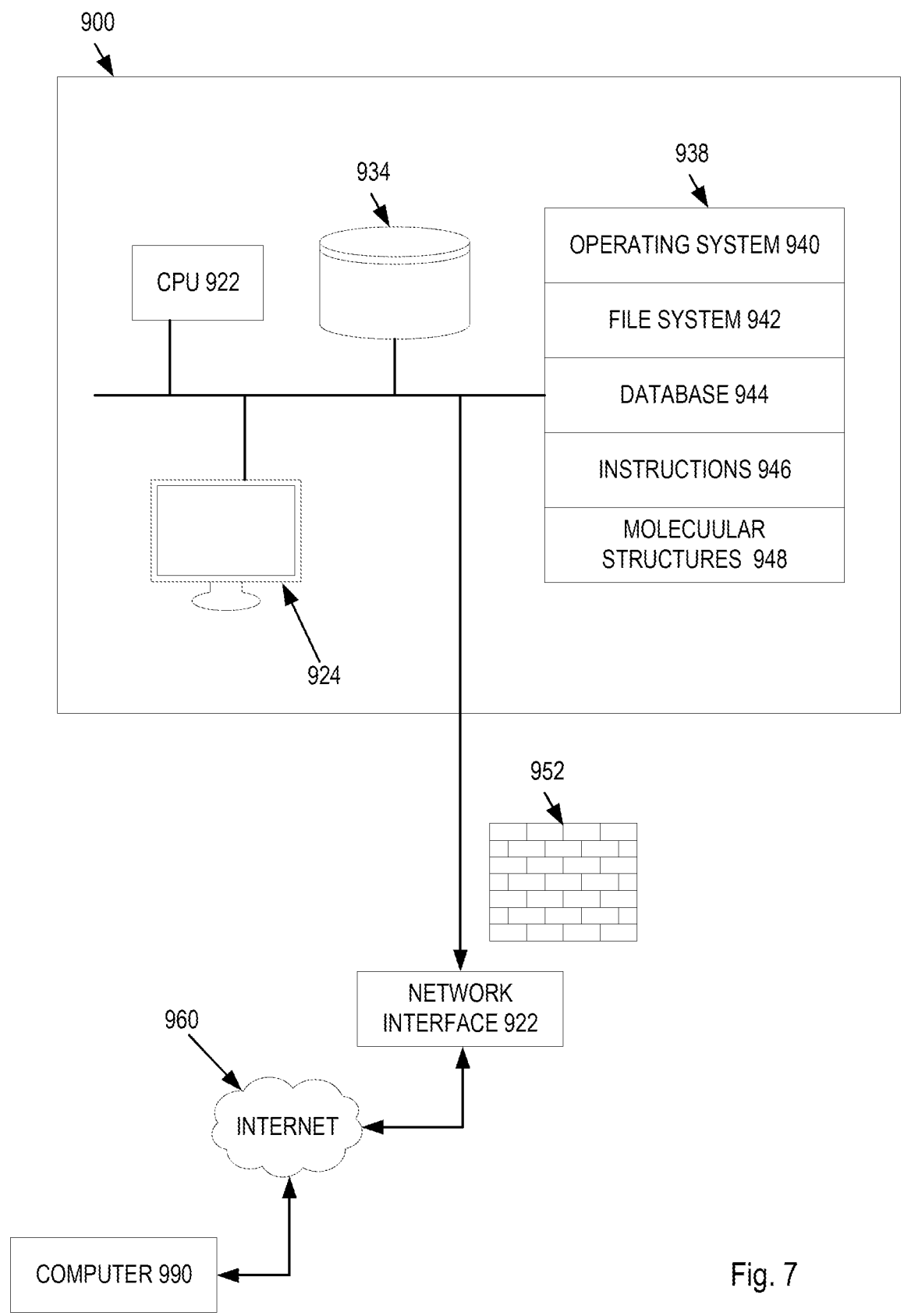
FIG. 7 is an illustration of one embodiment of an exemplary computer system.

An exemplary general-purpose computing apparatus (900) suitable for practicing methods described herein is depicted schematically in FIG. 7. Such a system could be used by any one or more party of the two or more parties who wish to simultaneously edit molecular structure data, as described herein.

The computer system (900) comprises at least one data processing unit (CPU) (922), a memory (938), which will typically include both high speed random access memory as well as non-volatile memory (such as one or more magnetic disk drives), a user interface (924), one more disks (934), and at least one network connection (936) or other communication interface for communicating with other computers over a network, including the Internet (960), as well as other devices, such as via a high speed networking cable, or a wireless connection. Network connection (936) can be used for two more users to communicate molecular structure data with one another, where each of the users has a computer system (990) (not shown) having similar capability to that computer system (900) and able to receive data to be shared from computer (900). There may optionally be a firewall (952) between the computer (900) and the Internet (960). At least the CPU (922), memory (938), user interface (924), disk (934) and network interface (936), communicate with one another via at least one communication bus (933).

Memory (938) stores procedures and data, typically including some or all of: an operating system (940) for providing basic system services; one or more application programs, such as a parser routine (950), and a compiler (not shown in FIG. 7), a file system (942), one or more databases (944) that store data such as molecular structures, and optionally a floating point coprocessor where necessary for carrying out high level mathematical operations such as for carrying out editing operations on molecular structures. The methods of the present technology may also draw upon functions contained in one or more dynamically linked libraries, not shown in FIG. 7, but stored either in memory (938), or on disk (934).

The database and other routines that are shown in FIG. 7 as stored in memory (938) may instead, optionally, be stored on disk (934) where the amount of data in the database is too great to be efficiently stored in memory (938). The database may also instead, or in part, be stored on one or more remote computers that communicate with computer system (900) through network interface (936).

Memory (938) is encoded with instructions (946) for at least: carrying out concurrent editing operations on one or more molecular structures 948. The instructions can further include programmed instructions displaying 2D and 3D representations of the molecular structures stored in the database, as desired. In many embodiments, the edits themselves are not calculated on the computer (900) that interacts directly with a user, but are performed on a different computer (not shown) and, e.g., transferred via network interface (936) to computer (900).

Various implementations of the technology herein can be contemplated, particularly as performed on one or more computing apparatuses (machines that can be programmed to perform arithmetic) of varying complexity, including, without limitation, workstations, PC's, laptops, notebooks, tablets, netbooks, and other mobile computing devices, including cell-phones, mobile phones, and personal digital assistants. The methods herein may further be susceptible to performance on quantum computers. The computing devices can have suitably configured processors, including, without limitation, graphics processors and math coprocessors, for running software that carries out the methods herein. In addition, certain computing functions are typically distributed across more than one computer so that, for example, one computer accepts input and instructions, and a second or additional computers receive the instructions via a network connection and carry out the processing at a remote location, and optionally communicate results or output back to the first computer. Thus, the methods herein are particularly susceptible to being performed in cloud-computing environments, where data is stored, temporarily or permanently, on one or more remote hosted arrays of data storage in a secure fashion so that the data is only visible to a specific account holder. In cloud computing environments, processing power of arrays of remote processors can also be harnessed to carry out manipulations on data stored in the cloud environment, such that the results of such manipulations are only known to a specific account holder and/or those it gives permission to access the manipulations.

Control of the computing apparatuses can be via a user interface (924), which may comprise a display, mouse, keyboard, and/or other items not shown in FIG. 7, such as a track-pad, track-ball, touch-screen, stylus, speech-recognition device, gesture-recognition technology, human fingerprint reader, or other input such as based on a user's eye-movement, or any subcombination or combination of inputs thereof.

In one embodiment, edits can be represented as QR-codes and displayed on, e.g., a mobile-phone interface; such codes can be swapped back and forth between individuals by optical scanning of each other's devices' screens. In this way any compromising of a means of communication, e.g., wireless, internet, near-field communication, can be avoided.

The manner of operation of the technology, when reduced to an embodiment as one or more software modules, functions, or subroutines, can be in a batch-mode—as on a stored database of molecular structures, processed in batches, or by interaction with a user who inputs specific instructions for a single molecular structure.

The calculations created by the technology herein, as well as the molecular structures themselves, can be displayed in tangible form, such as on one or more computer displays, such as a monitor, laptop display, or the screen of a tablet, notebook, netbook, or cellular phone. The molecular structures and edits thereto, can further be printed to paper form, stored as electronic files in a format for saving on a computer-readable medium or for transferring or sharing between computers, or projected onto a screen of an auditorium such as during a presentation.

Certain default settings can be built in to a computer-implementation, but the user can be given as much choice as he or she desires over the features that are used in carrying out concurrent edits to molecular structure data.

EXAMPLES

Example 1: Causal Tree for a Single Site

Figure 2:
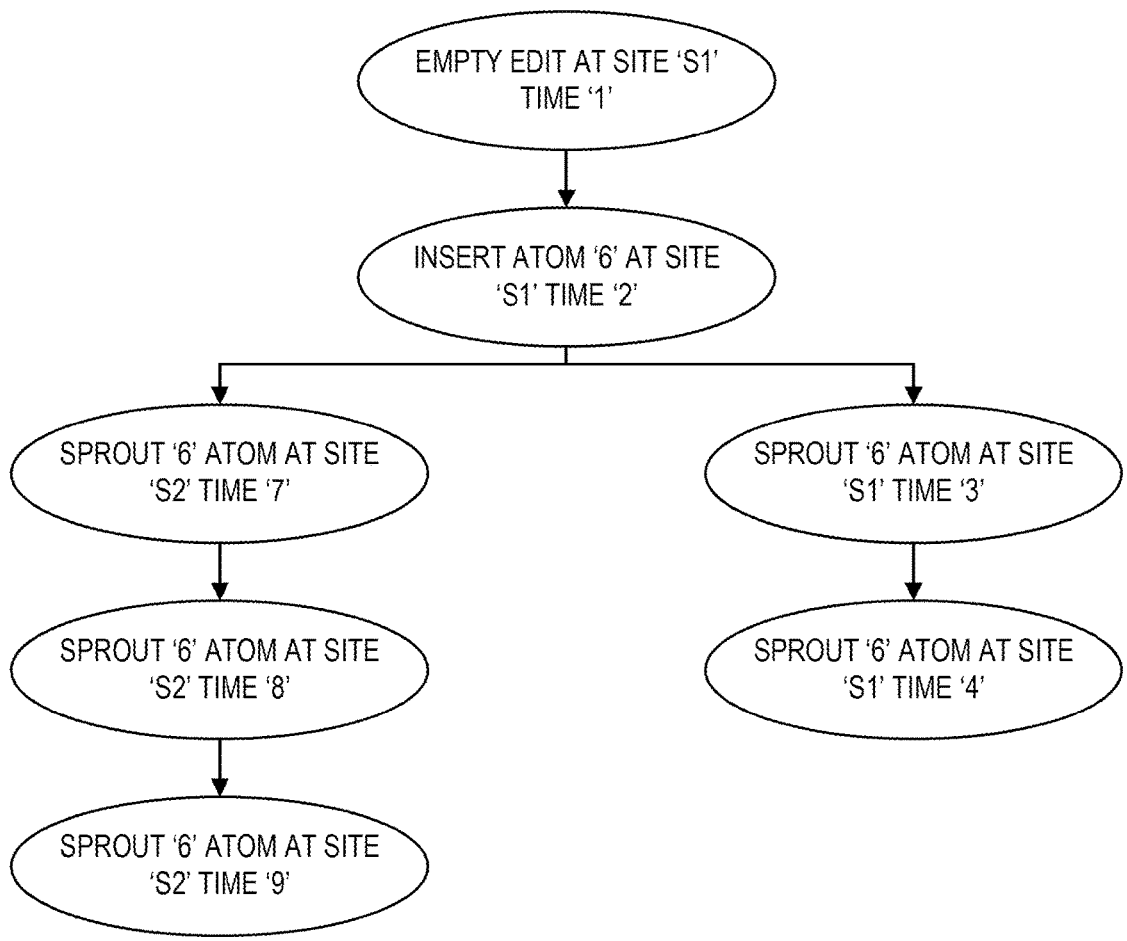
FIG. 2 is an illustration of one embodiment of edits by a second site on the tree of FIG. 1.
Figure 2:
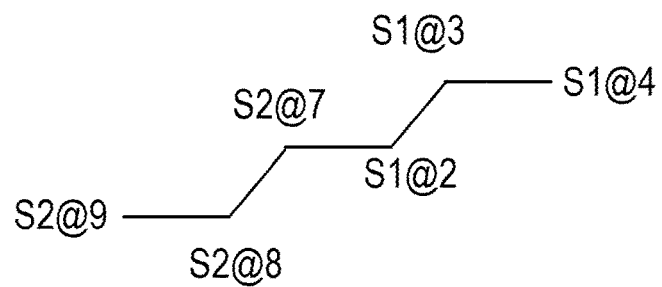

The example illustrated in FIG. 1 shows a simple causal tree for site 'S1', which has inserted a single carbon atom (note that the implicit empty edit which is common to all causal trees is included for clarity), followed by two edits which sprout carbon atom & bond pairs. The edits can be described as follows:

S1@1: (not shown) The initial empty edit (required for all new molecule CRDT's)
S1@2: Insert a carbon atom
S1@3: Sprout a single order bond from S1@2's atom bonded to a new carbon atom
S1@4: Sprout a single order bond from S1@3's atom bonded to a new carbon atom Example 2: Edits by a Second Site Continuing from Example 1, and illustrated in FIG. 2, site 'S1' sends its operational array to site 'S2'. Site 'S2' sprouts new atoms and bonds from the carbon atom inserted by site 'S1' at timestamp '2'. The new edits by S2 are summarized as follows.

Figure 3:
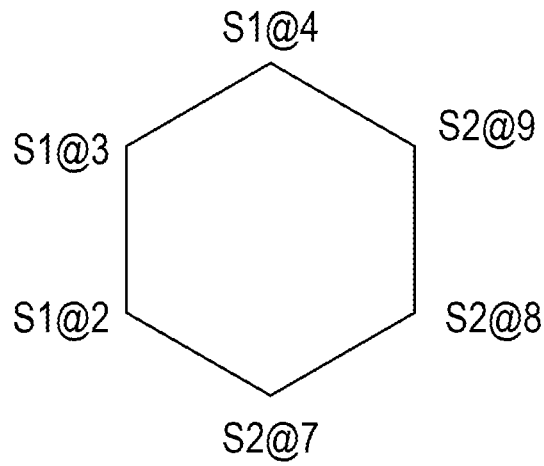
FIG. 3 is an illustration of one embodiment of site 'S2' communicating its edits back to site 'S1'.
Figure 3:
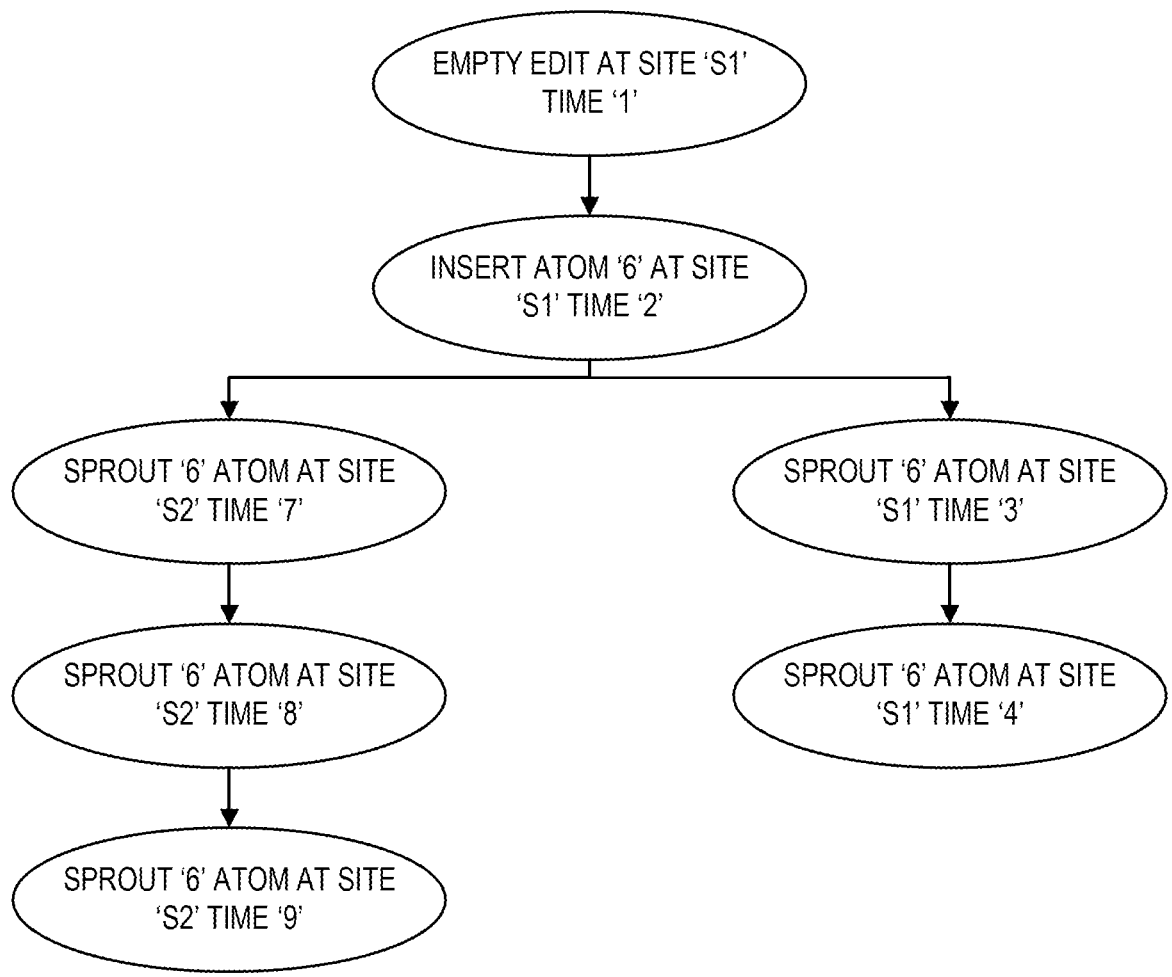

S2@7: Sprout a single order bond from S1@2's atom bonded to a new carbon atom
S2@8: Sprout a single order bond from S2@7's atom bonded to a new carbon atom
S2@9: Sprout a single order bond from S2@8's atom bonded to a new carbon atom Now, site 'S2' sends its operational array back to site 'S1', and site 'S1' makes new edits, as shown in FIG. 3.

Continuing from the previous edits of sites 'S1' and 'S2', site 'S1' adds a new single edit: S1@12: Adds a bond between the atoms from S2@9 and S1@4.

Note that this forms a ring, instead of the chain which was previously depicted. Also note that, unlike textual causal trees, this requires some edits to have more than one causal parent. Also note that the child branches between S1@2 and S1@12 are concurrent edits, though they are not in conflict.

Figure 4:
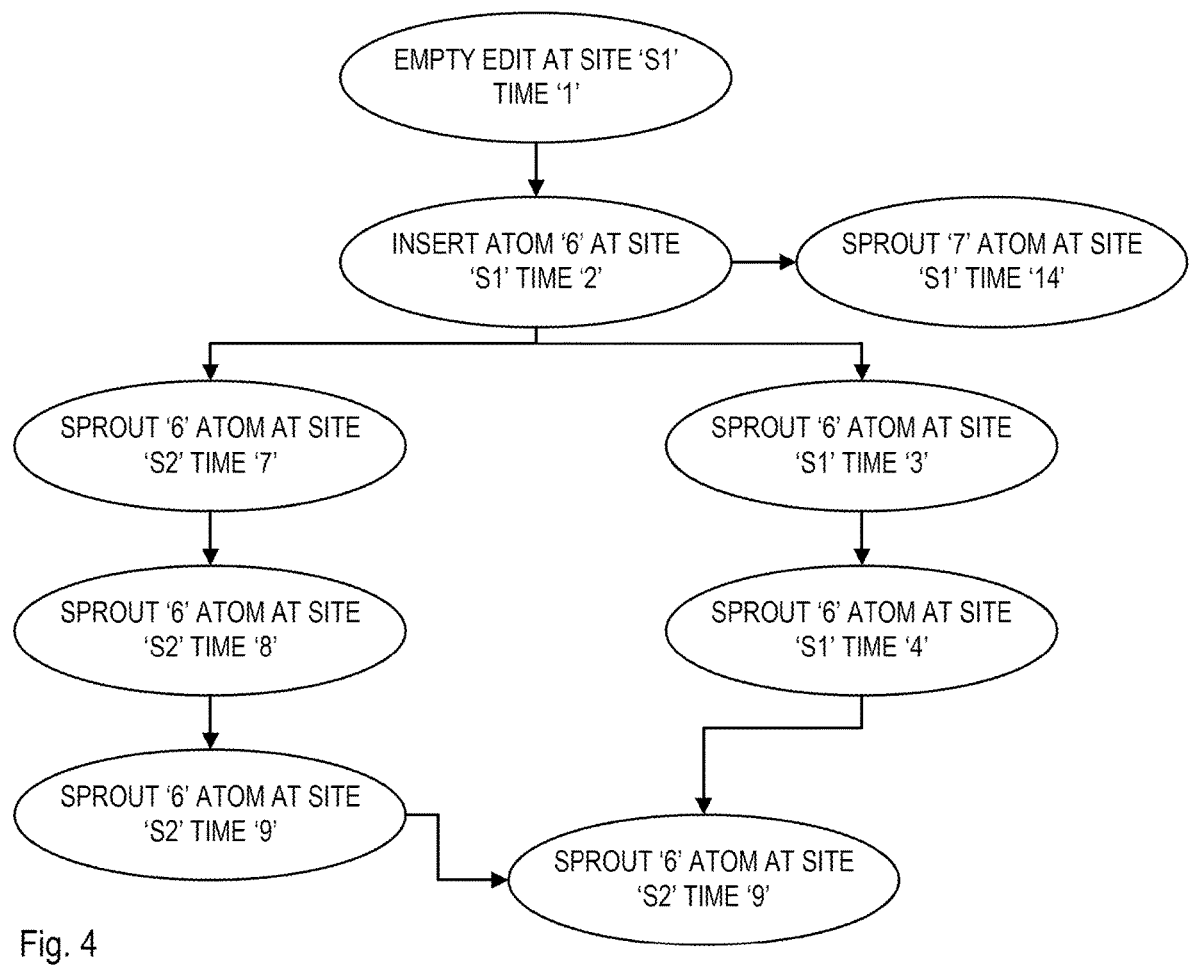
FIG. 4: is an illustration of one embodiment of S1 and S2 making simultaneous edits.

Now FIG. 4 shows site 'S1' and site 'S2' making simultaneous edits which are concurrent and would be in conflict using a data structure which is not a CRDT.

Site 'S1' again sends it operational array to site 'S2', then makes a new edit: S1@14: Sprout a single order bond from S1 @2's atom bonded to a new carbon atom.

Figure 5:
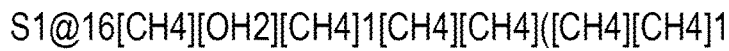
FIG. 5: is an illustration of one embodiment of S2 making new edits concurrently with S1.
Figure 5:
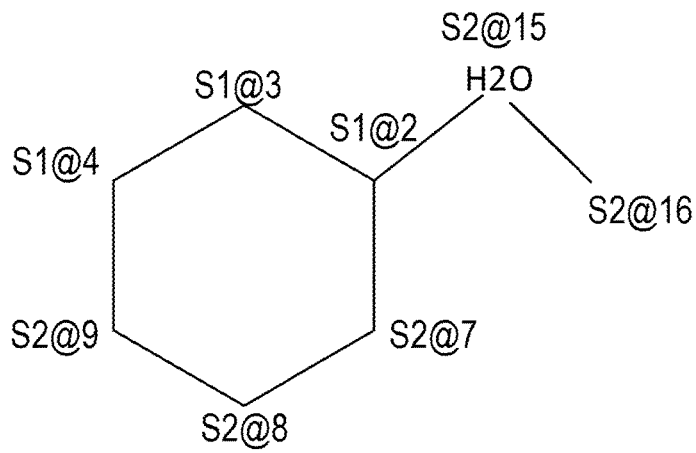
Figure 5:
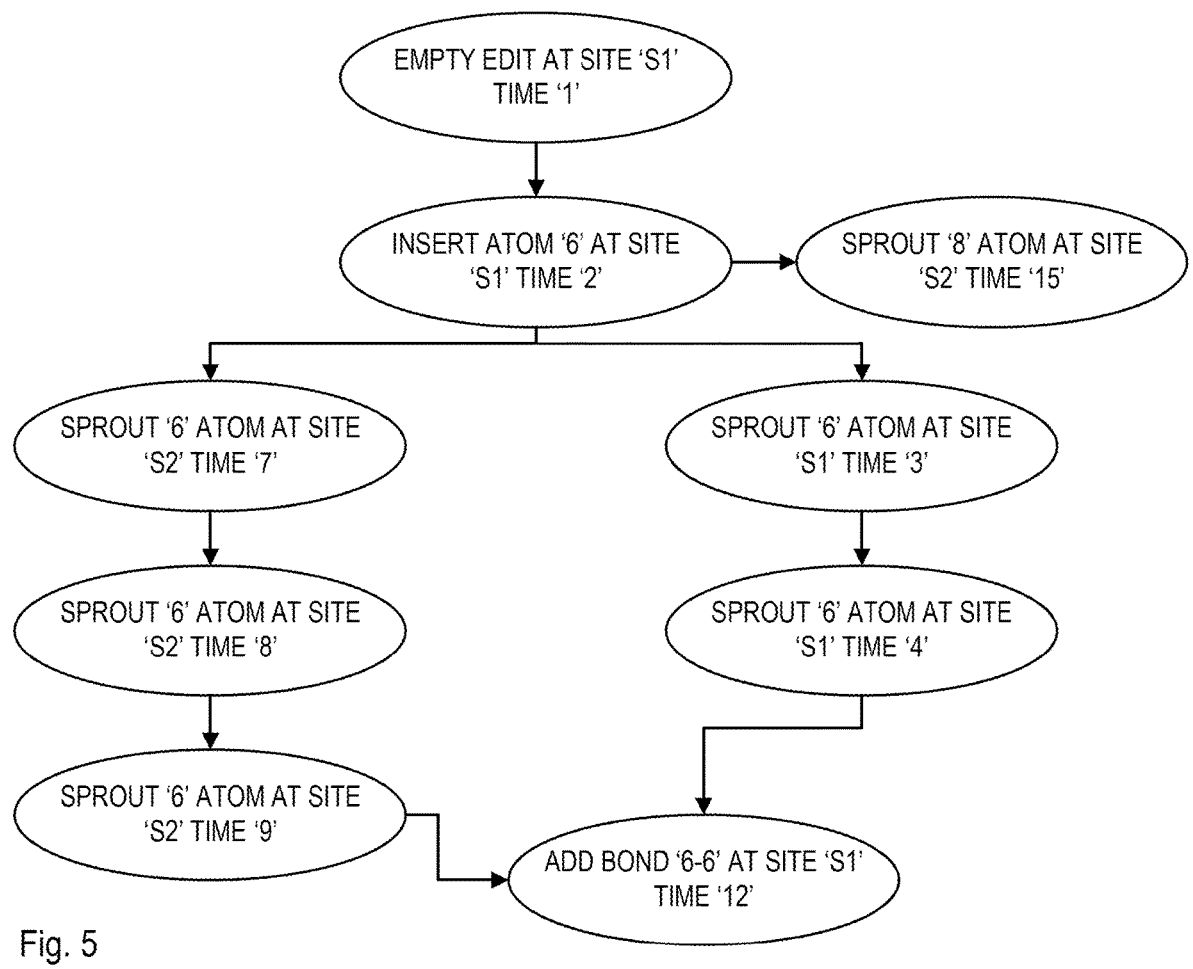

As shown in FIG. 5, Site 'S2' makes new edits concurrently with site 'S1':

S2@15: Sprout a single order bond from S1@2's atom bonded to a new oxygen atom
S2@16: Sprout a single order bond from S2@15 's atom bonded to a new carbon atom Note that edits S2@15, S2@16 and S1@14 are commonly rooted at S1@2, and are concurrently applied on different sites ('S1' and 'S2').

Figure 6:
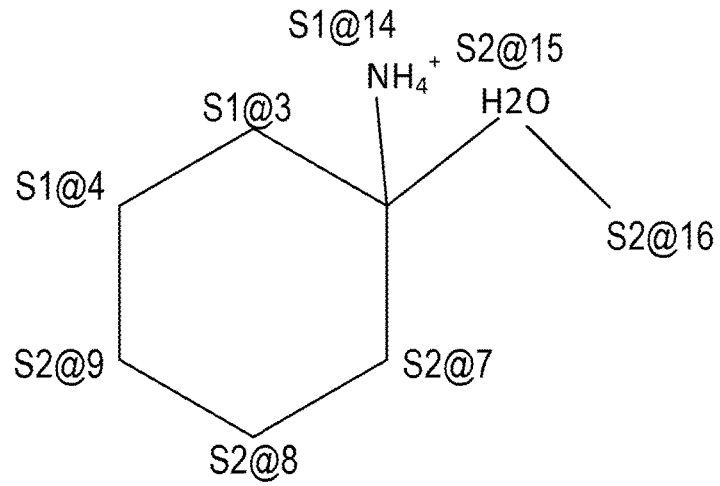
FIG. 6: is an illustration of one embodiment of S2 sending its operational array to S1.
Figure 6:
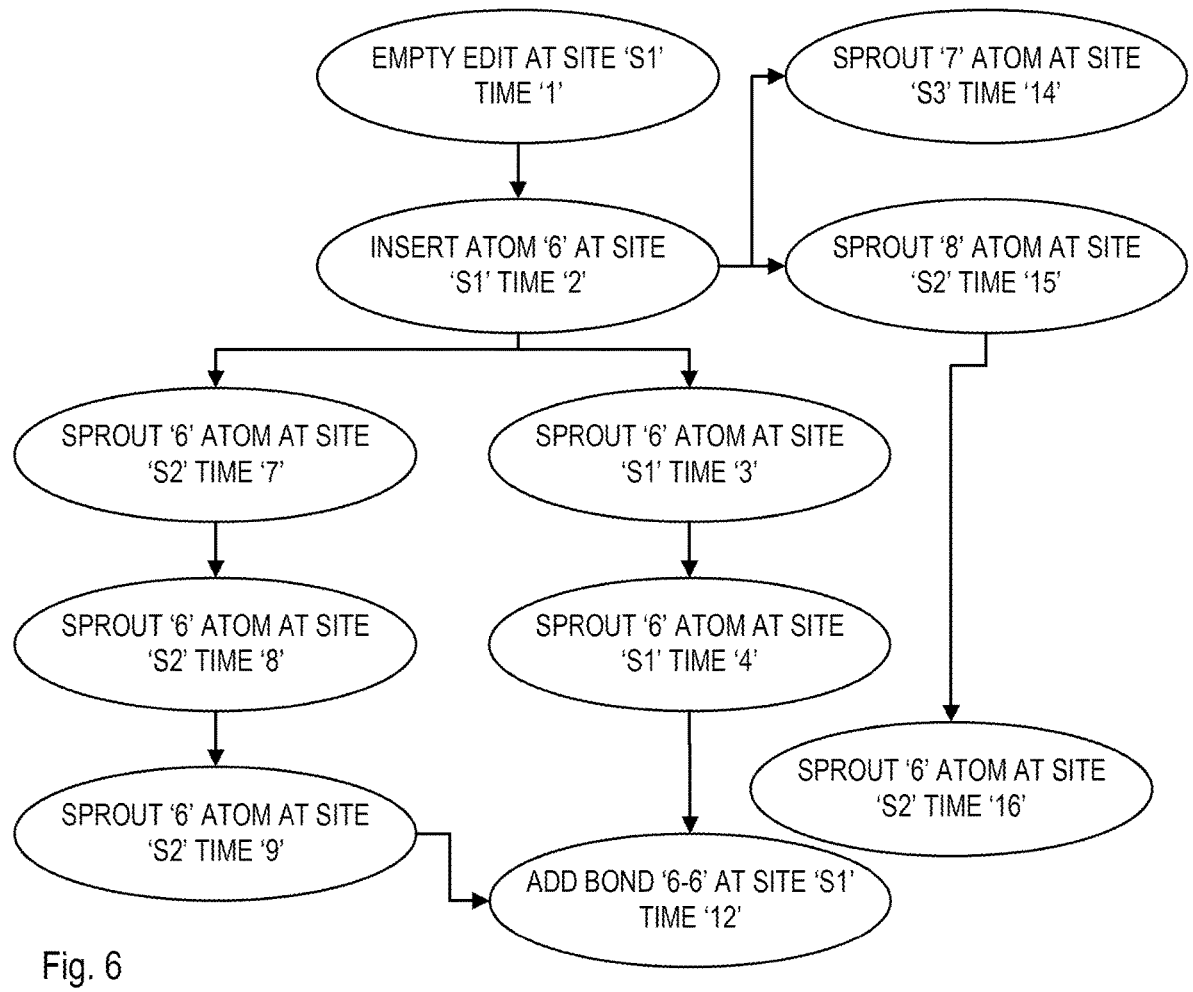

Finally, in FIG. 6, Site 'S2' now sends its operational array to site 'S1', which merges the new edits in without conflict. Now the edits are merged, and the original intent of both parties is preserved, and any invalid chemistry can be resolved with successive edits.

Example 3: Sample Code

The below-listed script is written in the programming language Python and will be intelligible to one skilled in the art of computer programming.

```
# each mol represents a user, where the uses are sharing a session
s1 = CRDTMol("S1")
s2 = CRDTMol("S2")
# first add_root_atom adds the first non empty causal entry
s1_root = s1.add_root_atom(OEElemNo_C)
# mutations return the causal atom, which can be used as a parent in subsequent mutations
cur = s1.sprout(OEElemNo_C, parent=s1_root)
s1_cur = s1.sprout(OEElemNo_C, parent=cur)
# we've sprouted two carbons in site 1, send those edits to site 2
s1.graph( ) .depict("site-1-step-1.png", s1.events[-1].timestamp.to_string( ) )
s1.send_to(s2)
# now site 2 makes edits, sprouting from the root
cur = s2.sprout(OEElemNo_C, parent=s1_root)
cur = s2.sprout(OEElemNo_C, parent=cur)
last = s2.sprout(OEElemNo_C, parent=cur)
s2.graph( ) .depict("site-2-step-2.png", s2.events[-1].timestamp.to_string( ) )
# now site 2 shares the edits with site 1
s2.send_to(s1)
s2.graph( ) .depict("site-1-step-3.png" , s2.events[-1].timestamp.to_string( ) )
# creates a bond between sprouted atoms of sites 1 and 2
s1.bond(s1_cur, last)
s2.graph( ) .depict("site-1-step-4.png", s2.events[-1].timestamp.to_string( ) )
```

```
# send the new edits to site 2
s1.send_to (s2)
# now sites 1 and 2 make conflicting edits
s1.sprout(OEElemNo_N, s1_root)
cur = s2.sprout(OEElemNo_O, s1_root)
s2.sprout(OEElemNo_C, cur)
s2.send_to(s1)
s2.graph( ) .depict("site-1-step-5.png" , s2.events[-
1].timestamp.to_string( ) )
```

The foregoing description is intended to illustrate various aspects of the instant technology. It is not intended that the examples presented herein limit the scope of the appended claims. The invention now being fully described, it will be apparent to one of ordinary skill in the art that many changes and modifications can be made thereto without departing from the spirit or scope of the appended claims.

What is claimed:

1. A non-transitory machine-readable medium having executable instructions to cause one or more processing units to perform a method of editing a molecular structure, the method comprising:
   receiving a plurality of edits to the molecular structure; and
   for each of the plurality of edits,
      timestamping that edit when the edit does not include a timestamp, wherein each of the plurality of edits for this molecular structure has a different timestamp, and
      updating a conflict-free data structure associated with the molecular structure using at least that edit, wherein the conflict-free data structure incorporates the plurality of edits that have been made to the molecular structure into a set of the ordered set of immutable edits.

2. The machine-readable medium of claim 1, wherein the plurality of edits includes at least one remotely generated edit that was generated by device different from the device receiving the plurality of edits.

3. The machine-readable medium of claim 1, wherein the timestamping comprises timestamping the edit with a Lamport timestamp.

4. The machine-readable medium of claim 3, wherein the Lamport timestamp uses at least a Lamport logical clock.

5. The machine-readable medium of claim 1, wherein the timestamping comprises:
   incrementing a clock; and
   timestamping the edit using a current value of the clock.

6. The machine-readable medium of claim 1, wherein each of the plurality of edits has a unique identifier.

7. The machine-readable medium of claim 1, wherein each of the plurality of edits is at least one of adding an atom, deleting an atom, adding a bond, deleting a bond, changing an atom characteristic, and changing a bond characteristic.

8. The machine-readable medium of claim 1, further comprising:
   cryptographically signing each of the plurality of the edits that were locally generated such that an authorship of each of the plurality of edits can be verified.

9. The machine-readable medium of claim 1, wherein each of the plurality of edits has a parent edit.

10. The machine-readable medium of claim 1, further comprising:
    ordering the plurality of edits using at least the timestamp of each of the plurality of edits.

11. The machine-readable medium of claim 1, further comprising:
    sending a locally generated edit to a molecule device, where the molecule device propagates that edit to another device.

12. A method of editing a molecular structure, the method comprising:
    receiving a plurality of edits to the molecular structure from; and
    for each of the plurality of edits,
       timestamping that edit when the edit does not include a timestamp, wherein each of the plurality of edits for this molecular structure has a different timestamp, and
       updating a conflict-free data structure associated with the molecular structure using at least that edit, wherein the conflict-free data structure incorporates the plurality of edits that have been made to the molecular structure into a set of the ordered set of immutable edits.

13. The method of claim 12, wherein the plurality of edits includes at least one remotely generated edit that was generated by device different from the device receiving the plurality of edits.

14. The method of claim 12, wherein the timestamping comprises timestamping the edit with a Lamport timestamp.

15. The method of claim 14, wherein the Lamport timestamp uses at least a Lamport logical clock.

16. The method of claim 12, wherein the timestamping comprises:
    incrementing a clock; and
    timestamping the edit using a current value of the clock.

17. The method of claim 12, wherein each of the plurality of edits has a unique identifier.

18. The method of claim 12, wherein each of the plurality of edits is at least one of adding an atom, deleting an atom, adding a bond, deleting a bond, change an atom characteristic, and change a bond characteristic.

19. The method of claim 12, further comprising:
    cryptographically signing each of the plurality of the edits that were locally generated such that an authorship of each of the plurality of edits can be verified.

20. The method of claim 12, wherein each of the plurality of edits has a parent edit.

* * * * *